United States Patent [19]

Felger

[11] Patent Number: 4,517,176
[45] Date of Patent: May 14, 1985

[54] ANTICHOLINERGIC GLUCURONIDE COMPOUNDS AND ANTIPERSPIRANT USE THEREOF

[75] Inventor: Carl B. Felger, College Park, Md.

[73] Assignee: The Gillette Company, Boston, Mass.

[21] Appl. No.: 504,018

[22] Filed: Jun. 13, 1983

[51] Int. Cl.$^3$ .................. A61K 7/32; A61K 7/34; A61K 7/38; A61K 9/12
[52] U.S. Cl. .................. 424/47; 424/DIG. 5; 424/66; 424/67; 424/68; 424/69; 514/770; 514/941; 514/969
[58] Field of Search ............... 424/65, 68, 47, DIG. 5

[56] References Cited

U.S. PATENT DOCUMENTS

| | | | |
|---|---|---|---|
| 3,312,709 | 4/1967 | MacMillan | 424/65 X |
| 3,326,768 | 6/1967 | MacMillan | 424/65 |
| 3,527,864 | 9/1970 | MacMillan et al. | 424/65 X |
| 3,624,200 | 11/1971 | Moffett | 424/65 |
| 3,678,156 | 7/1972 | MacMillan et al. | 424/65 |
| 3,767,786 | 10/1973 | MacMillan | 424/65 |
| 3,775,538 | 11/1973 | DeSalva et al. | 424/65 |
| 3,833,592 | 9/1974 | Papanastassiou et al. | 424/65 |
| 3,839,345 | 10/1974 | Pars et al. | 424/65 |
| 3,953,599 | 4/1976 | MacMillan | 424/65 |

FOREIGN PATENT DOCUMENTS

| | | | |
|---|---|---|---|
| 2401489 | 7/1975 | Fed. Rep. of Germany | 424/65 |
| 2523866 | 12/1976 | Fed. Rep. of Germany | 424/65 |

*Primary Examiner*—Dale R. Ore
*Attorney, Agent, or Firm*—Leonard J. Janowski

[57] ABSTRACT

This invention relates to the preparation and use of glucuronide derivatives of anticholinergic compounds to render them safe for use in the control of human perspiration. These derivatives, which lack mydriatic potency in the eye, are applied to the axillae where they are rendered biologically active by the action of β-glucuronidase occurring naturally on the skin.

6 Claims, No Drawings

ANTICHOLINERGIC GLUCURONIDE COMPOUNDS AND ANTIPERSPIRANT USE THEREOF

BACKGROUND OF THE INVENTION

It is well known to those conversant with the physiology of perspiration that there are involved two distinct glandular species; the eccrine sweat glands and the aprocrine sweat glands. The eccrine sweat gland is found in generalized distribution over the human body surface with the average person having over two million glands. These glands produce water which contains salt and minerals, their main function being control of body temperature by evaporative cooling. The major quantity of sweat produced by the body is eccrine sweat.

The apocrine sweat gland is found primarily in the axillae and on the hair-covered regions of the body. The gland itself is somewhat larger than the eccrine sweat gland and generally opens into the hair follicle at a point above the level of the sebaceous gland opening rather than directly on the skin surface as does the eccrine gland. Apocrine sweat is a whitish, odorless liquid which contains considerable amounts of lipid materials as compared to eccrine sweat which contains over 99% water.

Up to the present time, the most widely used antiperspirant compositions intended for topical application to control the rate of eccrine perspiration have included a variety of metal salts capable of inhibiting the flow of perspiration by what has been described as an astringent action. These salts are thought to react with skin proteins, causing coagulation and concomitant swelling, resulting in the partial blockage of the external openings of the sweat gland and the reduction in the flow of sweat. In addition, these salts act as antimicrobial agents, preventing bacteria of the surface of the skin from acting on the lipid content of aprocine sweat to form objectionably odorous products.

In most of the commercial antiperspirant compositions on the market, the active antiperspirant ingredient is usually an astringent salt of aluminum, zinc, zirconium or rare earth metal. Such salts are generally not maximally effective antiperspirants upon first use and often require a number of applications over a period of time to reach a desired level of antiperspirant activity. The salts also tend to react with the skin and change its chemical composition. Therefore, work has been undertaken to discover compounds which will act rapidly to afford the desired antiperspirant activity, without the need for a series of applications to obtain useful antiperspirant effects. Of course, such products should also be harmless to clothing and the skin.

Anticholinergic compounds such as atropine and scopolamine have been used in the treatment of certain pathological cases of excessive perspiration. The eccrine sweat glands, which secrete most of the liquid sweat, are activated by a chemical "mediator" which is liberated at nerve endings when they are properly stimulated. This "mediator" is thought to be acetylcholine. Anticholinergic compounds reduce perspiration by interfering with the action of acetylcholine, probably by blocking the receptor sites of the secretory cells of the sweat glands.

Although the potential utility of anticholinergic compounds in over-the-counter antiperspirant formulations has long been recognized, such utilization has been retarded because the classic anticholinergics do not provide adequate inhibition of perspiration at a level of usage which is physiologically safe. Only recently have relatively safe and effective antiperspirant formulations based on anticholinergic compounds been investigated. Some such formulations, disclosed in British Pat. No. 940,279, contain certain anticholinergic scopolamine esters as active ingredients. Although the antiperspirant formulations of the British patent are said to be highly effective, the anticholinergic compounds employed therein can hydrolyze and the formulations thereby lose activity over protracted periods of time.

An improvement in the use of the scopolamine esters mentioned above is described in U.S. Pat. Nos. 3,312,709 and 3,326,768, in which para-(lower)alkoxybenzoyl esters of scopolamine or acid salts thereof are employed in compositions described as having improved anticholinergic and antiperspirant properties. Additional disclosures of antiperspirant formulations based on anticholinergic compounds are found in U.S. Pat. No. 3,624,200 and U.S. Pat. No. 3,767,786, also dealing with esters of scopolamine.

It is well known that anticholinergic compounds of the types discussed above have a mydriatic effect. This mydriatic effect, though desirable in conjunction with an eye examination by an eye doctor, is an undesirable property for an antiperspirant because an accidental transfer of an anticholinergic antiperspirant to the eye can represent a significant safety problem.

As exemplified by the above-mentioned U.S. patents, the predominant anticholinergics evaluated for antiperspirant use are scopolamine and its esters. Though the efficacy of scopolamine and its esters was demonstrated over twenty years ago, it is apparent that these compounds have not achieved widespread use as antiperspirants. This lack of use may be related to the mydriatic property referred to above, and, additionally, to the fact that ester-containing anticholinergics such as scopolamine may be cleaved by esterase activity in human perspiration, thus rendering the anticholinergic ineffective as an antiperspirant.

The problems of esterase inactivation and mydriasis, discussed above, have been overcome by the use of the novel glucuronide compounds of the subject invention.

BRIEF SUMMARY OF THE INVENTION

I have discovered that scopolamine and other anticholinergic compounds having primary alcohol groups may be rendered safe for use in the control of human perspiration by converting them into their O-glucuronic acid derivatives. These derivatives, which lack mydriatic potency in the eye, are applied to the axilla where they are rendered biologically active by the action of β-glucuronidase occuring naturally on the skin.

DETAILED DESCRIPTION OF THE INVENTION

The preparation of of O-β-D-glucuronic acid derivates has been carried out by a number of different techniques. Chemical synthesis typically involves condensation of a suitable protected aglycon with an alkyl(2,3,4-tri-O-acetyl-β-D-glucopyranosyl halide)-glucuronate followed by deprotection of the glucuronide and aglycon (Ando, K., Suzuki, S., and Arita, M. [1970] J. Antibiotics 23, 408; Sarett, L. H., Strachan, R. G., and Hirschmass, R. F. [1966] U.S. Pat. No. 3,240,777). A second approach involves feeding large amounts of the aglycon to animals, collecting their urine and isolating the glucuronide (Hornke, I., Fehlhaber, H. W., Uihlein, M. [1979] U.S. Pat. No. 4,153,697). Alternatively, the animal can be sacrificed and the bile isolated from its gall bladder, from which the glucuronide is purified (DeLuca, H. F., Schnoes, H. K., and LeVan, L. W. [1981] U.S. Pat. No. 4,292,250). This in vivo synthesis is catalyzed by the class of enzymes known as uridine diphosphoglucuronyl transferases. In vitro use of this enzyme to produce various β-glucuronides has been reported; for example, a phenolic compound has been glucuronidated (Johnson, D. B., Swanson, M. J., Barker, C. W., Fanska, C. B., and Murrill, E. E. [1979] Prep. Biochem. 9, 391).

An in vitro enzymatic process for the synthesis of β-glucuronides has several advantages over prior art chemical synthesis or animal feeding methods. Chemical synthesis requires a minimum of four steps: (1) protection of all the nucleophilic groups in the aglycon except the one involved in the glycosidic linkage, (2) preparation of a suitably protected reactive derivative of D-glucuronic acid, e.g., methyl(2,3,4-tri-O-acetyl-β-D-glucopyranosyl halide)glucuronate, (3) condensation, and (4) deprotection. Complications arise if the aglycon contains functional groups sensitive to the conditions of deprotection. For example, aglycons containing esters or other alkali-sensitive linkages can be hydrolyzed during the saponification of the methyl and acetyl protecting groups. In contrast, an in vitro enzymatic process involves a direct condensation between a readily available cofactor and the aglycon.

The animal feeding approach to making β-glucuronides also has several disadvantages as compared to an in vitro enzymatic method. The most significant disadvantage is that stringent purification is required. Other disadvantages are the inconvenience of maintaining animals, and other metabolic pathways including hydroxylation, alkylation, and sulfation can compete with glucuronidation, thus resulting in low yields of the desired product.

The preferred process for preparing the β-glucuronides used in the practice of this invention is an in vitro enzymatic process comprising incubating liver microsomes at a suitable temperature in the presence of a suitable buffer at a suitable pH with an anticholinergic agent and uridine 5'-diphosphoglucuronic acid for a sufficient time to conjugate the aglycon with glucuronic acid after which the essentially pure salt is isolated from the reaction mixture.

When it is desired to prepare glucuronides of ester-containing anticholinergics such as scopolamine, it is necessary to first remove all or substantially all of the esterase activity from liver microsomes. These esterases are removed since they will hydrolyze the aglycon and/or its glucuronic acid derivative. This operation can be done by washing the liver microsomes in a suitable buffer, as described herein, or by other equivalent washing means known to persons in this art. Advantageously, an esterase inhibitor can be used to supplement the washing of the microsomes. For example, a competitive inhibitor of the esterases such as lysine ethyl ester, and the like, or a suicide substrate such as phenylmethylsulfonyl fluoride, and the like, can be used. The thus obtained liver microsomes are then incubated for a sufficient length of time with the following:

(1) a suitable buffer to maintain the pH at about 7 to about 8.5;

(2) an ester-containing anticholinergic having a primary alcohol; and (3) UDPGA (uridine 5'-diphosphoglucuronic acid).

A sufficient length of time for incubation is that which allows the conjugation of the aglycon with glucuronic acid.

The enzymatic reaction, described herein, can be carried out over a pH range of about 7 to about 8.5 with different buffer strengths and with various buffers, for example, sodium N-2-hydroxyethyl piperazine-N'-2-ethanesulfonic acid, tris hydrochloride, and the like. Quantitative glucuronidation can be obtained by increasing the amount of UDP glucuronic acid in the reaction.

The chromatographic methods described herein are based on reversed phase liquid chromatography on C-18 silica supports. This technique is well suited for the purification of enzymatically-produced glucuronides of hydrophobic compounds. Unreacted aglycon is much more hydrophobic than the corresponding glucuronide and thus will be well resolved on reversed phase systems. The cofactor, UDP glucuronic acid, the enzymes, and the byproduct, UDP, are all very hydrophilic and will be much less retained than the glucuronide of a hydrophobic compound. Finally, all the solvent systems described are based on ammonium acetate, an easily removable buffer. Modifications to this system may be necessary in order to purify glucuronides of very hydrophilic compounds. Other reversed phase stationary supports, for example, phenyl silica, C-8 silica, and the like, can be used. The resolution of the two diastereomers is enhanced when the pH is lowered from 7.0 to 3.7, which would increase the fraction of the molecules in the zwitterionic form necessary for an intramolecular ionic interaction. In addition, increasing the ionic strength from 0.1% NH$_4$OAc to 1% NH$_4$OAc diminishes the resolution as would be expected if an intramolecular "salt bridge" were present.

Liver microsomes, which can be used in the subject invention, can be obtained from mammalian sources, for example, rabbit, bovine, and the like.

The temperature of incubation in the enzymatic step can be from about 20° to about 45° C.

The following examples are illustrative of the process and products of the invention, but are not to be construed as limiting. All percentages are by weight and all solvent mixture proportions are by volume unless otherwise noted.

EXAMPLE 1

Enzymatic preparation of (+,−)-tropicamide O-β-D-glucuronic acid

Four grams of a rabbit liver or bovine liver microsomal fraction (Sigma Chemical Co., St. Louis, Mo.) are suspended in 100 ml of a 75 mM tris hydrochloride buffer (ph=7.5–8.0). The microsomes are suspended by repeatedly drawing the mixture through a pipette tip. The microsomes are then pelleted by centrifugation at 100,000 g for 30 minutes. The supernatant is discarded, and the pellet is resuspended at 100 ml with a 150 mM tris hydrochloride (pH=7.5–8.0) solution, containing 200 mg (+,−)-tropicamide (Hoffman-LaRoche, Nutley, N.J., also disclosed in U.S. Pat. No. 2,726,245) and 1 gram of sodium uridine 5'-diphosphoglucuronic acid (Sigma Chemical Co.). After a 20-hour incubation at 37° C., the reaction is terminated by heating to about 70° C., and centrifuging the reaction mixture. The desired product is in the supernatant. The yield of desired product is determined by high performance liquid chromatography (HPLC) to be ~75%.

The HPLC conditions are as follows: a 0.39×30 cm C-18μ Bondapak column (Waters Associates, Milford, Mass.) is eluted at 2 ml/min. with 0.1% NH4OAc (pH=5.75). After injection of the sample, a linear gradient to 60% methanol is applied to the column over a 20 minute period. The column eluant is monitored with an ultraviolet detector set at 254 nm. Under these conditions the reaction product elutes as a partially resolved doublet. On the basis of the chemical and spectral data presented below the two peaks are assigned as (+)-tropicamide O-β-D-glucuronic acid and (−)-tropicamide O-β-D-glucuronic acid.

EXAMPLE 2

Isolation of essentially pure (+), (−)-tropicamide O-β-D-glucuronic acid

The pH of the reaction mixture, obtained in Example 1, is adjusted to 5.75 with 1.26 ml of 10% NH4OAc (pH=5.75); 25 ml of methanol is added to the reaction, and the suspension is centrifuged at 44,000 g for 60 minutes. The supernatant is collected and located onto a 15 mm by 250 cm column of octadecyl derivatized silica (50-100 micron particles) (Waters Associates) which had been equilibrated with an 80/20 solution of 0.1% NH4OAc (pH=5.75)/methanol. The column is washed at 3 ml/min. until the absorbance of the eluant at 254 nm is less than 0.05. Essentially pure (+),(−)-tropicamide O-β-D-glucuronic acid is then eluted with a 55/45 solution of 0.1% NH4OAc (pH=5.57)/methanol. Unreacted (+,−)-tropicamide is eluted from the column with a 40/60 solution of 0.1% NH4OAc (pH=5.75)/methanol. The desired product contains less than 1% of (+,−)-tropicamide contamination.

(+),(−)-Tropicamide O-β-D-glucuronic acid has the following formula:

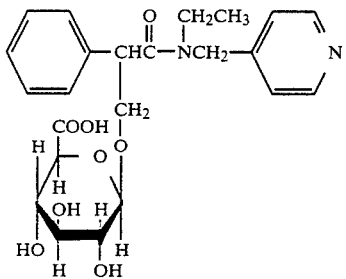

EXAMPLE 3

Preparation of scopolamine O-β-D-glucuronic acid

Four hundred milligrams of a rabbit liver or bovine liver microsomal fraction (Sigma Chemical Co., St. Louis, Mo.), containing uridine 5'-diphosphoglucuronyl transferase is suspended in 20 ml of a 75 mM tris HCl buffer (pH=8.0). The microsomes are suspended by repeatedly drawing the mixture through a pipette tip. The microsomes are then pelleted by centrifugation at 44,000 g for 20 minutes. The supernatant is discarded, the pellet washed a second time, and the pellet resuspended to 10 ml with a 75 mM tris HCl (pH=8.0) solution containing 20 mg scopolamine (Sigma) and 140 mg of sodium uridine 5'-diphosphoglucuronic acid (Sigma). In addition, the reaction mixture contains either 100 mM lysine ethyl ester (Sigma) or 10 μM phenylmethylsulfonyl fluoride (PMSF) (Sigma) which had been predissolved in a small volume of propanol immediately before addition. After a 20 hour incubation at 37° C., the reaction is terminated by heating the sample for two minutes at 70° C., followed by centrifugation at 44,000 g for 20 minutes. The supernatant is removed and analyzed by high performance liquid chromatography (HPLC). The yield of desired product is determined to be ~95%.

The HPLC conditions are as follows: a 0.39×30 cm C-18μ Bondapak column (Waters Associates, Milford, Mass.) is eluted at 2 ml/min. with 0.1% NH4OAc (pH=7.5). After injection of the sample, a linear gradient to 60% methanol is applied to the column over a 20-minute period. The column eluant is monitored with an ultraviolet detector set at 254 nm. Under these conditions, the reaction product has a retention time of 12 minutes, whereas scopolamine has a retention time of 18 minutes. On the basis of the chemical and spectral data presented below, the product is assigned as scopolamine O- -D-glucuronic acid.

Scopolamine O-β-D-glucuronic acid has the following structure:

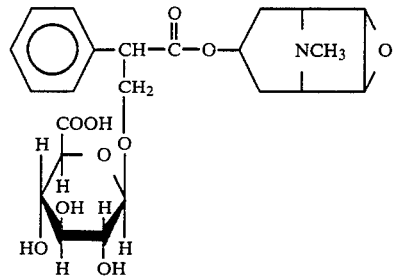

EXAMPLE 4

Preparation of hyoscyamine O-β-D-glucuronic acid

The reaction conditions are identical to those utilized for scopolamine in Example 3. The concentration of hyoscyamine is 2 mg/ml and the reaction is carried out for 20 hours.

EXAMPLE 5

Isolation of scopolamine O-β-D-glucuronic acid and hyoscyamine O-β-D-glucuronic acid The glucuronides are isolated with the HPLC system described above. Typically, 25 μl of 1% NH4OAc (pH=7.5) is added to 225 μl of the reaction supernatant, and the entire sample is injected. Larger amounts can be prepared with a preparative chromatography system.

Hyoscyamine O-β-D-glucuronic acid has the following structure:

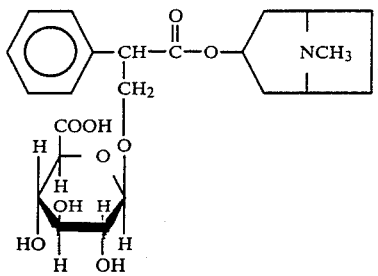

EXAMPLE 6

Upon substituting atropine for hyoscyamine in Example 5, there is obtained atropine O-β-D-glucuronic acid having the following structure:

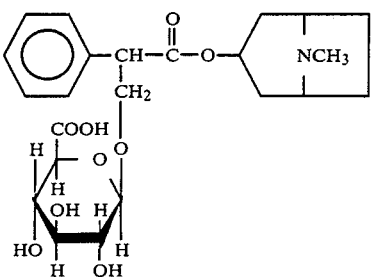

EXAMPLE 7

Upon substituting other ester-containing anticholinergics having a primary alcohol for scopolamine in Example 1, there are obtained the corresponding ester-containing anticholinergic O-β-D-glucuronic acids.

EXAMPLE 8

Salts with both inorganic and organic bases can be formed with the free acid of the compounds of the subject invention. For example, in addition to the ammonium salt, there also can be formed the sodium, potassium, calcium, and the like salts, by neutralizing an aqueous solution of the free acid with the corresponding base. The ammonium and other base salts of the compounds of the subject invention are useful in the same manner as the free acid form.

The concentration of anticholinergic glucuronide or acid addition salt employed in topical compositions for application to the human body should be consistent with the requirements of efficacy, safety and economy. These requirements can often be met with extremely small amounts of active ingredient, e.g., a small but perceptible amount of as little as about 0.1% by weight. We prefer to employ from 2–5% by weight although up to 20% by weight may be employed if desired. As indicated heretofore, the present compositions can include the aforementioned principal active ingredients either alone or in combination with other active materials. Accordingly, other antiperspirants such as the aluminum salts, zinc salts and zirconium salts (e.g., the chlorides, chlorhydroxides and sulfates) in concentrations of from about 5 to about 25 percent can be employed as supplementary active ingredients. Additionally, combinations of the said principal active ingredients with antibacterial agents suitable for topical deodorant use without inactivating glucuronidase offer a balanced approach to the problem. Such combinations include substances capable of minimizing bacterial action on available organic secretions in the affected areas, thereby supplementing the primary activity. The known antibacterials with demonstrated effectiveness in this function are appropriate for use in the present compositions.

Dermatologically acceptable carriers into which the active ingredients can be incorporated to produce satisfactory antiperspirant compositions, as indicated heretofore, are those commonly employed for topical application of cosmetics or pharmaceuticals. Such carriers or vehicles include lotions, ointments, aerosols, water solutions, creams (preferably of the oil-in-water type), pulverulent mixtures, gelled sticks and the like. Depending on the physical nature of the vehicle or carrier employed, the method of this invention can be practiced by applying such compositions topically from a roll-on applicator, by a brush or pad, by sprinkling on the skin, from a squeeze bottle, by spraying under propellant pressure, and in other manners according to the particular type of carrier employed.

In preparing the desired product form of the present compositions, various additives, diluents and adjuvants can be utilized. These illustratively include perfumes, essential oils, surfactants (e.g. polysorbate 80, polyoxyethylene sorbitan trioleate, sodium lauryl sulfate, sodium cetyl sulfate), emulsifiers, (e.g., glyceryl monostearate-diethylaminoethyl alkyl amide phosphate, isopropyl myristate, cetyl alcohol, glyceryl and glycol esters of stearic acid), alcohols (e.g., ethanol and isopropanol), glycols (e.g., propylene glycol, glycerol, sorbitol), ointment-type bases (e.g., spermaceti, carbowaxes, beeswax), higher fatty acids (e.g., stearic acid, palmitic acid), propellants (e.g., halogenated hydrocarbons, carbon dioxide, nitrogen), silicone-type fluids (e.g. polysiloxane fluid), and solid diluents (e.g. calcium carbonate, starch, bentonite, talc).

EXAMPLE 9

Cream Antiperspirant Composition

A cream antiperspirant composition is prepared by mixing together the ingredients of the following recipe in which the parts are by weight.

| Ingredient | Parts |
| --- | --- |
| Condensate of ethylene oxide with a hydrophobic base formed by condensing propylene oxide with propylene glycol (Pluronic F-68) | 5.0 |
| Tropicamide O—β-D-glucuronic acid | 1.0 |
| Cetyl trimethyl ammonium bromide | 0.5 |
| Cetyl alcohol | 1.0 |
| Glyceryl monostearate | 13.0 |
| Spermaceti wax | 4.0 |
| Glycerine | 3.0 |
| Polyoxyalkylene propylene glycol monostearate | 0.5 |
| Polyoxyalkylene stearate | 0.5 |
| Ethanol | 10.0 |
| Perfume | 0.1 |
| Water, q.s. | |

The foregoing composition when used daily is effective in reducing axillary perspiration. Repeated applications have less tendency to cause irritation to the skin than do similar compositions containing conventional astringent antiperspirants, similarly causing less irritation when applied to freshly shaved areas of the skin.

EXAMPLE 10

Lotion Antiperspirant Composition

The following lotion composition is prepared in which the parts are by weight:

| Ingredient | Parts |
| --- | --- |
| Condensate of ethylene oxide with a hydrophobic base formed by condensing propylene oxide with propylene glycol (Pluronic F-68) | 10.0 |
| Scopolamine O—β-D-glucuronic acid | 2.0 |
| 8-hydroxyquinoline sulfate | 0.8 |
| Ethanol | 5.0 |
| Veegum | 3.5 |
| Mineral oil | 6.0 |
| Stearyl alcohol | 1.5 |
| Polyoxyalkylene propylene glycol monostearate | 0.8 |
| Polyoxyalkylene stearate | 0.8 |
| Perfume | 0.1 |
| Water, q.s. | |

The composition when applied to the skin produces results similar to those obtained with the composition of Example 9.

EXAMPLE 11

Liquid Antiperspirant Composition

The following liquid antiperspirant composition is prepared in which the parts are by weight.

| Ingredient | Parts |
| --- | --- |
| Condensate of ethylene oxide with a hydrophobic base formed by condensing propylene oxide with propylene glycol (Pluronic F-68) | 10.0 |
| Hyoscyamine O—β-D-glucuronic acid | 5.0 |
| Aluminum chlorhydrol | 10.0 |
| Glycerine | 5.0 |
| Ethanol | 32.0 |
| Benzyl-dimethyl-alkyl ammonium chloride containing 8 to 18 carbon atoms in the alkyl group | 0.1 |
| Perfume | 0.1 |
| Water, q.s. | |

When the composition is applied to the skin, the results obtained are similar to those obtained with the composition of Example 9.

EXAMPLE 12

Antiperspirant Stick Deodorant

An antiperspirant (and deodorant) in stick form is prepared by mixing together the following ingredients at elevated temperature, then pouring the composition into a mold and allowing it to solidify. The quantity of each ingredient in parts by weight is given below:

| Ingredient | Parts |
| --- | --- |
| Condensate of ethylene oxide with a hydrophobic base formed by condensing propylene oxide with propylene glycol (Pluronic F-68) | 2.0 |
| Atropine O—β-D-glucuronic acid | 4.0 |
| Sodium stearate | 8.5 |
| Propylene glycol | 5.0 |
| Cetyl trimethyl ammonium bromide | 0.5 |
| Perfume | 0.1 |
| Ethyl alcohol, q.s. | |

When rubbed on the skin, the stick provides similar results as were obtained with the composition of Example 9.

EXAMPLE 13

Aerosol Antiperspirant

| Ingredient | Parts |
| --- | --- |
| Aluminum chlorhydrol | 11.9 |
| Scopolamine O—β-D-glucuronic acid, ammonium salt | 3.0 |
| Isopropyl myristate | 2.0 |
| Volatile silicone | 11.0 |
| Bentone | 1.0 |
| Ethyl alcohol | 2.0 |
| Perfume | 0.1 |

The above composition is packaged in a pressure container in the conventional manner along with 77 parts of a conventional liquified gaseous propellant.

When the liquid is sprayed upon the skin in the usual manner upon release from the pressurized package, it is found to be effective as an antiperspirant in the same manner as the compositions of the preceding examples.

While particular embodiments of the invention have been described, it will be apparent to those skilled in the art that variations may be made thereto without departing from the spirit of the invention and the scope of the appended claims.

What is claimed is:

1. An antiperspirant composition comprising about 0.1% by weight up to 20% by weight of a material selected from the group consisting of the O-β-D-glucuronide of anticholinergic compounds having a primary alcohol and base acid addition salts thereof, incorporated into a dermatologically acceptable carrier lotions, ointments, aerosols, water solutions, creams, pulverulent mixtures and gelled sticks.

2. An antiperspirant composition as described in claim 1 in which the concentration of glucuronide is from about 2-5%.

3. An antiperspirant composition as described in claim 1 in which the anticholinergic compound is selected from the group comprising (+),(−)-tropicamide, scopolamine, hyoscyamine, and atropine.

4. The process of inhibiting perspiration which comprises the step of applying to the human body a composition comprising at least 0.1% by weight of a material selected from the group consisting of the O-β-D-glucuronic acids of anticholinergic compounds having a primary alcohol, and base addition salts thereof, incorporated into a dermatologically acceptable carrier lotions, ointments, aerosols, water solutions, creams, pulverulent mixtures and gelled sticks.

5. The process of inhibiting perspiration as described in claim 4 in which the composition comprises about 2-5% of the glucuronide.

6. The process of inhibiting perspiration as described in claim 4 in which the anticholinergic compound is selected from the group comprising (+),(−)-tropicamide, scopolamine, hyoscyamine, and atropine.

* * * * *